(12) United States Patent
Reisman et al.

(10) Patent No.: US 10,117,568 B2
(45) Date of Patent: Nov. 6, 2018

(54) GEOGRAPHIC ATROPHY IDENTIFICATION AND MEASUREMENT

(71) Applicant: Kabushiki Kaisha TOPCON, Tokyo (JP)

(72) Inventors: Charles A. Reisman, Mamaroneck, NY (US); Qi Yang, Foster City, CA (US)

(73) Assignee: Kabushiki Kaisha TOPCON, Tokyo (JP)

( * ) Notice: Subject to any disclaimer, the term of this patent is extended or adjusted under 35 U.S.C. 154(b) by 132 days.

(21) Appl. No.: 14/990,340

(22) Filed: Jan. 7, 2016

(65) Prior Publication Data
US 2016/0206190 A1 Jul. 21, 2016

Related U.S. Application Data

(60) Provisional application No. 62/103,935, filed on Jan. 15, 2015.

(51) Int. Cl.
*A61B 3/00* (2006.01)
*A61B 3/10* (2006.01)
(Continued)

(52) U.S. Cl.
CPC ............ *A61B 3/0025* (2013.01); *A61B 3/102* (2013.01); *A61B 3/1225* (2013.01); *A61B 3/14* (2013.01);
(Continued)

(58) Field of Classification Search
None
See application file for complete search history.

(56) References Cited

U.S. PATENT DOCUMENTS 6,293,674 B1 9/2001 Huang et al.
7,222,961 B2 5/2007 Soliz et al.
(Continued)

FOREIGN PATENT DOCUMENTS

EP 2763103 A2 8/2014
JP 2011072716 A 4/2011
(Continued)

OTHER PUBLICATIONS

Faber, Dirk J. et al. "Quantitative measurement of attenuation coefficients of weakly scattering media using optical coherence tomography" In: Optics Express, Sep. 20, 2004, vol. 12, No. 19, pp. 4353-4365.
(Continued)

*Primary Examiner* — Tsung-Yin Tsai
(74) *Attorney, Agent, or Firm* — Pearne & Gordon LLP

(57) ABSTRACT

Geographic atrophy of the eye can be detected and measured by imaging the eye at a depth greater than the retinal pigment epithelium (RPE) at a plurality of locations of the eye, for example, using optical coherence tomography (OCT); determining a ratio of the intensities of imaging signals of a retinal layer(s) with respect to the intensity of imaging signals of a sub-RPE layer(s) at each location; determining representative values based at least in part on the determined ratios; generating a map of the representative values; and identifying diseased areas from the map. Contours and binary maps may be generated based on the identified diseased areas. The size and shape of the identified areas may be analyzed and monitored over a period of time to phenotype subjects and classify diseases.

28 Claims, 14 Drawing Sheets

(51) Int. Cl.
*A61B 3/14* (2006.01)
*A61B 3/12* (2006.01)
*G06T 7/00* (2017.01)

(52) U.S. Cl.
CPC .. *G06T 7/0012* (2013.01); *G06T 2207/10101* (2013.01); *G06T 2207/30041* (2013.01)

(56) References Cited

U.S. PATENT DOCUMENTS

| | | |
|---|---|---|
| 7,301,644 B2 | 11/2007 | Knighton et al. |
| 7,505,142 B2 | 3/2009 | Knighton et al. |
| 7,512,436 B2 | 3/2009 | Petty et al. |
| 7,659,990 B2 | 2/2010 | Knighton et al. |
| 7,668,342 B2 | 2/2010 | Everett et al. |
| 7,768,652 B2 | 8/2010 | Everett |
| 7,924,429 B2 | 4/2011 | Knighton et al. |
| 8,045,176 B2 | 10/2011 | Everett et al. |
| 8,073,202 B2 | 12/2011 | Everett et al. |
| 8,208,688 B2 | 6/2012 | Everett et al. |
| 8,319,974 B2 | 11/2012 | Knighton et al. |
| 8,332,016 B2 | 12/2012 | Stetson |
| 8,416,991 B2 | 4/2013 | Everett et al. |
| 8,913,793 B2 | 12/2014 | Everett et al. |
| 9,179,834 B2* | 11/2015 | Reisman ............... G06T 7/0012 |
| 9,517,005 B2* | 12/2016 | Reisman ............... G06T 7/0012 |
| 9,526,412 B2 | 12/2016 | Yang et al. |
| 2007/0291277 A1* | 12/2007 | Everett .................. A61B 3/102 356/497 |
| 2009/0180123 A1 | 7/2009 | Knighton et al. |
| 2010/0226542 A1 | 9/2010 | Everett et al. |
| 2010/0290007 A1* | 11/2010 | Van de Velde ........ A61B 3/102 351/221 |
| 2012/0271288 A1 | 10/2012 | Marziliano et al. |
| 2012/0274896 A1 | 11/2012 | Vermeer et al. |
| 2012/0274898 A1 | 11/2012 | Sadda et al. |
| 2013/0094720 A1 | 4/2013 | Stetson |
| 2013/0242259 A1* | 9/2013 | Hacker .................. A61B 3/102 351/206 |
| 2013/0286354 A1 | 10/2013 | Stetson et al. |
| 2014/0357991 A1* | 12/2014 | Wilder Smith ...... A61B 5/4848 600/427 |
| 2015/0201829 A1* | 7/2015 | Yang .................. G01N 21/4795 382/131 |

FOREIGN PATENT DOCUMENTS

| | | |
|---|---|---|
| JP | 2013542840 | 11/2013 |
| JP | 2014516646 A | 7/2014 |

OTHER PUBLICATIONS

Van Der Meer, F.J., "Vascular applications of quantitative optical coherence tomography" In: Downloaded from UvA-DARE, the institutional repository of the University of Amsterdam (UvA), Nov. 1, 2005.

Xu, Chenyang et al. "Characterization of atherosclerosis plaques by measuring both backscattering and attenuation coefficients in optical coherence tomography" In: Journal of Biomedical Optics, May/Jun. 2008. vol. 13, No. 3, pp. 034003-1-034003-8.

Vermeer, K.A. et al. "Retinal Nerve Fiber Layer Attenuation Coefficient Maps Derived From Volumetric OCT Data" In: Rotterdam Ophthalmic Institute, No. 798, May 6, 2012.

Van Der Schoot, Josine et al., "The Effect of Glaucoma on the Optical Attenuation Coefficient of the Retinal Nerve Fiber Layer in Spectral Domain Optical Coherence Tomography Images" In: Investigative Ophthalmology and Visual Science, Apr. 2012, vol. 53, No. 4 pp. 2424-2430.

Vermeer, K. A. et al. "RPE-Normalized RNFL Attenuation Coefficient Maps Derived from Volumetric OCT Imaging for Glaucoma Assessment" In: Investigative Ophthalmology and Visual Science, Sep. 2012, vol. 53, No. 10 pp. 6102-6108.

Vermeer, K.A. et al. "Quantitative RNFL attenuation coefficient measurements by RPE-normalized OCT data" In: Proceedings of SPIE, vol. 8209, Feb. 2012, pp. 82090U1-82090U-6.

Euopean Search Report for EP 14 15 3444 dated Oct. 27, 2014.

"Semi-automatic geographic atrophy segmentation for SD-OCT images"; Qiang Chen, Luis de Sisternes, Theodore Leng, Luoluo Zheng, Lauren Kutzscher and Daniel L. Rubin; Biomedical Optics Express 2730; Published Nov. 1, 2013 (c) 2013 OSA Dec. 1, 2013, vol. 4, No. 12.

"Morphometric Analysis of Bruch's Membrane, the Choriocapillaris, and the Choroid in Aging"; Raan S. Ramrattan, Theo L. van der Schaft, Cornelia M. Mooy, Wim C. de Bruijn, Paul G.H. Mulder and Paulus T.V.M. de Jong; Investigative Ophthalmology & Visual Science, May 1004, vol. 35, No. 6; Copyright—Association for Research in Vision and Ophthalmology.

Spectral Domain Optical Coherence Tomographic Imaging of Geographic Atrophy; Brandon J. Lujan, MD, Philip J. Rosenfeld, MD, Phd, Giovanni Gregori, PhD, Fenghua Wang, MD; Robert W. Knighton, PhD, William J. Feuer, MS, Carmen A. Puliafito, MD, MBA; Imaging, Clinical Science; Ophthalmic Surgery, Lasers & Imaging; Mar./Apr. 2009; vol. 40, No. 2.

Spectral Domain Optical Coherence Tomography Imaging of Geographic Atrophy Margins; Srilaxmi Bearelly, MD, MHS, Felix Y. Chau, MD; Anjum Koreishi, BSE, Sandra S. Stinnett, DrPH; Joseph A. Izatt, PhD, Cynthia A. Toth, MD: Copyright 2009 by the American Academy of Ophthalmology; Published by Elsevier Inc.

"In vivo retinal optical coherence tomography at 1040 nm—enhanced penetration into the choroid"; A. Unterhuger, B. Povazay, B. Hermann and H. Saltmann; Copyright 2005 Optical Society of America; Published May 2, 2005/vol. 13, No. 9/Optics Express 3253.

"OCT Minimum Intensity as a Predictor of Geographic Atrophy Enlargement"; Paul F. Stetson, Zohar Yehoshua, Carlos Alexandre A. Garcia Filho, Renata Portella Nunes, Giovanni Gregori and Philip J. Rosenfeld; Investigative Ophthalmology & Visual Science; Copyright 2014, The Association for Research in Vision and Ophthalmology, Inc.; Published Feb. 2014/vol. 55/No. 2.

European Ophthalmic Review, vol. 6, Issue 2, Summer 2012, Extract; Optical Coherence Tomography Imaging and Quantitative Assessment for Monitoring Dry Age-Related Macular Degeneration; Albert J. Augustin.

IOVS Papers in Press. Published on Nov. 21, 2013 as Manuscript iovs.13-12552; Copyright 2013 by The Association for Research in Vision and Ophthalmology, Inc.

Lesion Size Detection in Geographic Atrophy by Polarization-Sensitive Optical Coherence Tomography and Correlation to Coventional Imaging Techniques; Christopher Schutze, Matthias Bolz, Ramzi Sayegh, Bernhard Baumann, Michael Pircher, Erich Gotzinger, Christoph K. Hitzenberger and Ursula Schmidt-Erfurth; Investigative Ophthalmology & Visual Science, Jan. 2013, vol. 54, No. 1; Copyright 2013 The Association for Research in Vision and Ophthalmology, Inc.

Acta Ophthalmologica 2011; "Performance of OCT segmentation procedures to assess morphology and extension in geographic atrophy"; Christopher Schutze, Christian Ahlers, Stefan Sacu; Georgios Mylonas, Ramzi Sayegh, Isabelle Golbaz; Gerlinde Matt, Geraldine Stock and Ursula Schmidt-Erfurth; Department of Ophthalmology, Medical University Vienna, Vienna, Austria.

NIH Public Access; Author Manuscript; National Institute of Health; Published in final edited form as Ophthalmology Apr. 2011 118(4); Progression of Geographic Atrophy in Age-Related Macular Degeneration Imaged with Spectral Domain Optical Coherence Tomography.

Europe PMC Funders Group; Author Manuscript; J Biomed Opt. 2010; "Segmentation and quantification of retinal lesions in age-related macular degeneration using polarization-sensitive optical coherence tomography".

Clinical and Epidemiologic Research; "Semiautomated Image Processing Method for Identification and Quantification of Geographic Atrophy in Age-Related Macular Degeneration"; Investigative Ophthalmology & Visual Science, Sep. 2011, vol. 52, No. 10; Copyright 2011 The Association for Research in Vision and Ophthalmology, Inc.

(56) References Cited

OTHER PUBLICATIONS

European Search Report for EP application No. 15151937.8 dated Jun. 6, 2015.
Wojtkowski M., et al. "Three-dimensinal Retinal Imaging with High-Speed Ultrahigh-Resolution Optical Coherence Tomography" In: Ophthalmology;~, May 16, 2005, vol. 112, No. 10, pp. 1734-1746.
U.S. Office Action for U.S. Appl. No. 15/355,391 dated Jul. 17, 2017.
Ahlers, Christian et al. "Imaging of the Retinal Pigment Epithelium in Age Related Macular Degeneration Using Polarization Sensitive Optical Coherence Tomography" In: Investigative Opthalmology & Visual Science, Apr. 2010, vol. 51, No. 4, pp. 2149-2157.

* cited by examiner

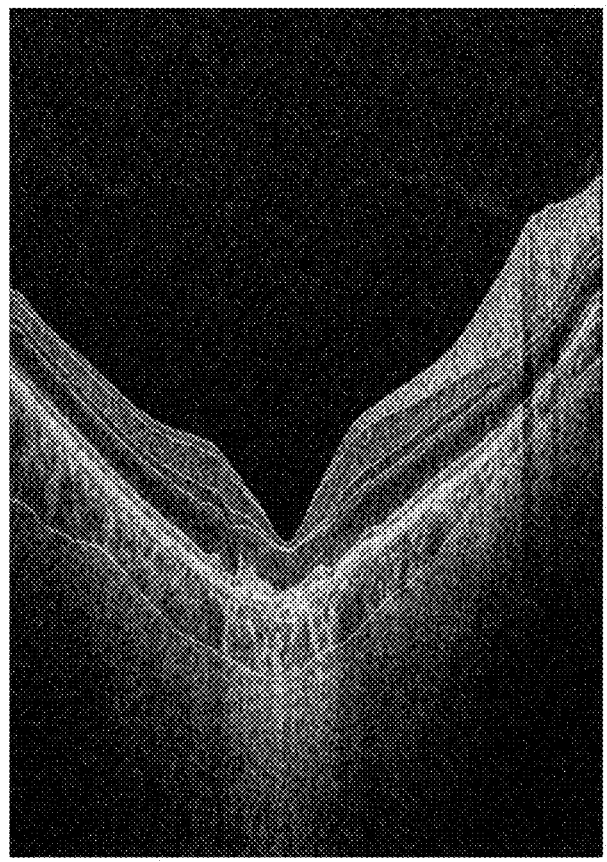
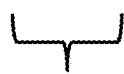
Figure 2B

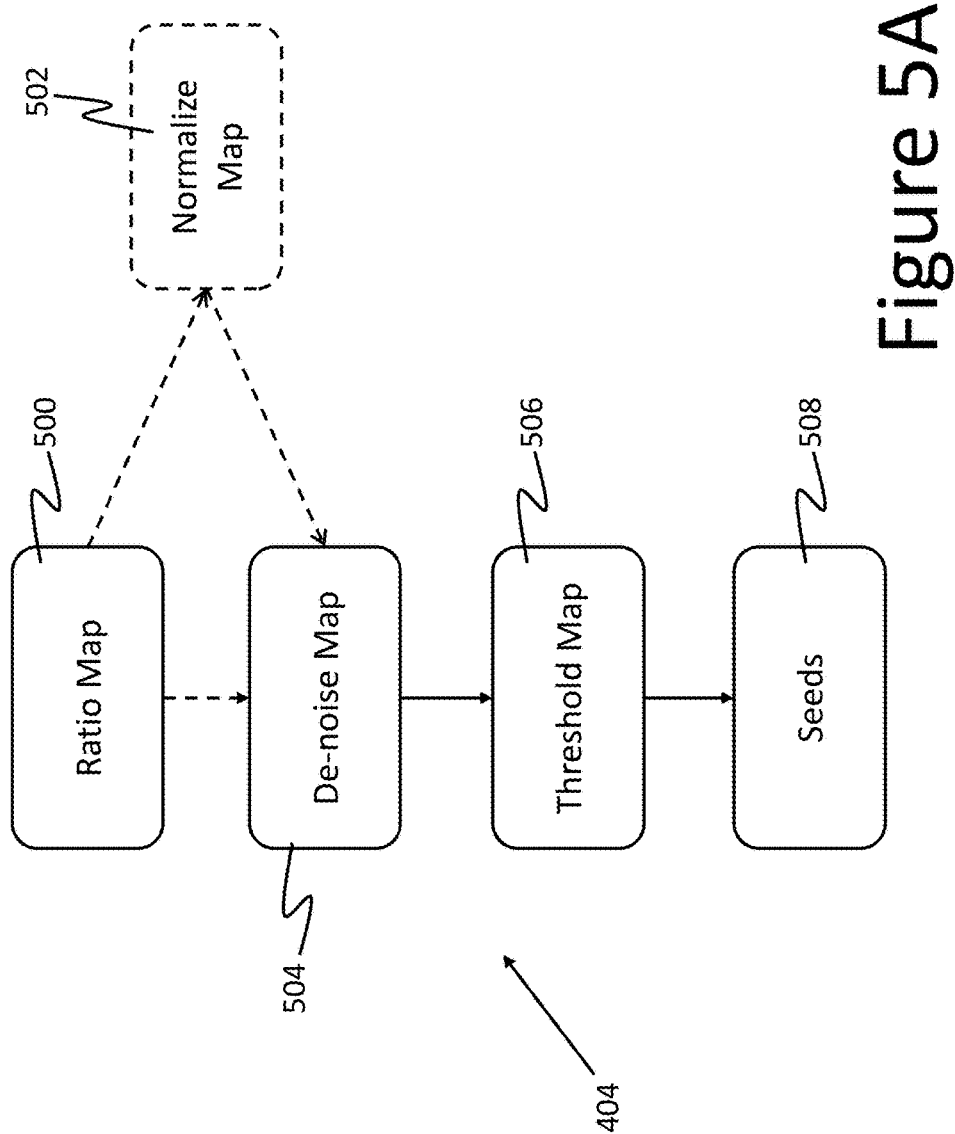

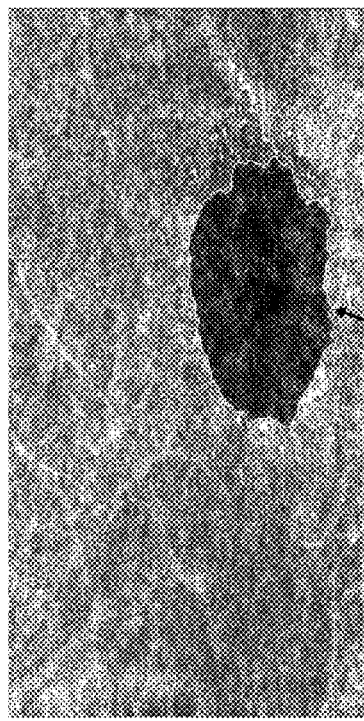

GEOGRAPHIC ATROPHY IDENTIFICATION AND MEASUREMENT

CROSS REFERENCE TO RELATED APPLICATIONS

This application claims priority to U.S. Provisional Application Ser. No. 62/103,935, filed on Jan. 15, 2015, entitled "GEOGRAPHIC ATROPHY IDENTIFICATION AND MEASUREMENT", the entirety of which is incorporated herein by reference.

BACKGROUND OF THE INVENTION

1. Field of the Invention

This application relates generally to the identification and measurement of geographic atrophy, and more specifically, to the identification of geographic atrophy in ophthalmic optical coherence tomography applications.

2. Description of Related Art

In ophthalmic and other applications, optical coherence tomography (OCT) is frequently used to generate three-dimensional scan data of a volume. OCT scans typically utilize one of relatively few fixation positions—most commonly the macula or optic disc, which place the respective feature at or near the center of the OCT scan. Wide scan patterns, which cover a large area that encompasses both the macula and optic disc, are also increasingly popular. A single scan in the axial dimension generates a depth profile (an "A-line" or "A-scan"), while a series of A-scans along a given line generate a B-scan. A series of B-scans can then be used to form the 3D volume.

In certain diseases of the back of the eye—such as geographic atrophy (GA), choroideremia, retinitis pigmentosa, glaucoma, and multiple sclerosis (MS—there are rough patterns of tissue atrophy that may present as either or both of: (1) changes in thickness; and (2) changes in OCT reflectivity values (image pixel intensities). Changes in thickness tend to result in thinning of the affected tissues with disease progression; however, less common retinal diseases related to inflammation can cause an increase in thickness. Diseases including GA, choroideremia, and retinitis pigmentosa involve atrophy of a layer or layers in the outer retina and/or surrounding tissue layers such as the retinal pigment epithelium (RPE), outer segments, inner segments, and/or choriocapillaris. Glaucoma and MS typically involve atrophy of the retinal nerve fiber layer (rNFL) and ganglion cell layer (GCL). Changes in OCT reflectivity values typically result from or are associated with a change in tissue attenuation properties, sometimes in a different tissue layer than the one being measured or observed. Alternatively and spuriously, decreases in reflectivity can result from increased shadowing (darkening, reducing the dynamic range of data) associated with lens crystallizations (cataracts) or floaters in the vitreous. Relatively large measurable changes are more associated with certain tissue layers and with certain retinal locations than with others, and the nature of these is highly disease specific.

Geographic atrophy, also called advanced 'dry' age-related macular degeneration (AMD), causes substantial and progressive visual impairment, developing in approximately 20% of patients presenting with preexisting clinical signs of AMD. GA is characterized by confluent areas of apoptosis at the level of photoreceptors and RPE atrophy, occurring bilaterally in more than half of patients affected. The condition progresses slowly over time, typically sparing the fovea until the later stages of disease progression. The atrophy can be unifocal (one atrophic spot) or multifocal (multiple spots).

Clinical trials to evaluate new therapies for non-neovascular AMD require reliable, accurate, and simple means of monitoring GA size and progression. Accurately monitoring GA progression can also help to better understand the pathogenesis of GA and AMD in general, as numerous aspects of AMD pathogenesis are not particularly well understood at present.

In choroideremia, the choriocapillaris (small capillary vessels in the choroid just outer to the Bruch's membrane), the RPE, and photoreceptors (in the later stages of disease) degenerate leading to lost visual function over time. As with GA, a visible thinning of the RPE can often be observed in affected areas in OCT scans. Additionally, due to decreased attenuation of the RPE layer (primarily of the RPE complex, though also of the choriocapillaris and possibly other tissue features, such as the photoreceptors), the signal in the choroid and beyond (e.g., the sclera) appears relatively bright in OCT scans.

Retinitis pigmentosa is a progressive retinal disease that affects the photoreceptors resulting in a severe loss of vision. Atrophy can be observed in the outer segments (OS) of receptor and other layers, such as the outer nuclear layer (ONL). Usually the thinning of the OS layer precedes changes in other receptor layers. In the case of RP, the visible thinning of the OS, possibly the RPE, ONL, and total retinal thickness can be observed with the NFL layer intact or even thicker.

There are four main processes in age-related macular degeneration pathogenesis, which preferentially affects the macula. In the first, lipofuscin formation, RPE metabolic insufficiency associated with aging leads to progressive accumulation of lipofuscin granules (a roughly even mixture of lipids and proteins) in the RPE. This is also related to failure to clear some metabolites from outer segment phagocytosis from the RPE. A lipofuscin component known as A2E is known to be a cytotoxic molecule, capable of generating free radicals, damaging DNA, etc.

Next, drusen formation is the result of extracellular deposits collecting between the RPE and Bruch's membrane. While most elderly individuals have a small number of "hard" drusen, the presence of numerous "hard" or "soft" drusen (especially the soft variety, which are typically larger in area), particularly when accompanied by pigment changes, is thought to be an early indicator of AMD. Drusen formation is also thought to relate to inflammatory processes as well as CFH gene allele Y402H.

The third process, chronic local inflammation, is not very well understood and is tied to lipofuscin and drusen formation, as well as additional factors including light irradiation and genetics, including the CFH gene allele Y402H.

Finally, neovascularization (wet AMD) is distinct from geographic atrophy. Neovascularization is thought to be preceded either by hypoxia or inflammation (or a combination of the two), leading to a signaling pathway that triggers an increased production of VEGF (vascular endothelial growth factor), which precipitates choroidal neovascularization.

Geographic atrophy is generally considered to be the non-wet end-stage of AMD, although some consider GA to be the default end-stage of advanced AMD. It should be noted, however, that both GA and wet AMD can occur together in the same eye. In GA, the RPE and outer segments atrophy in affected regions, and the atrophy typically extends to surrounding tissue layers as well, including the inner segments, the outer nuclear layer, and possibly the choriocapillaris. Associated with the loss of retinal function, blind spots (scotomas) result in the patient's central vision.

Traditional imaging modalities, fundus imaging and fundus autofluorescence imaging, have been used to detect GA. In fundus imaging, GA is defined as a sharply demarcated area exhibiting an apparent absence of the RPE, with visible choroidal vessels and no neovascular AMD. Fundus autofluorescence imaging is based on the autofluorescence properties of AMD-related compounds, such as lipofuscin, that build up in RPE cells. Fundus autofluorescence imaging is probably the most widely applied technique with respect to GA detection at present.

In an emerging OCT technique, GA is associated with increased OCT signal intensities in the choroidal region (i.e., outer to the Bruch's membrane), which arises from the absence of the RPE, other parts of the outer retina, and possibly the choriocapillaris. The RPE and choriocapillaris are two tissue layers, hyperreflective in OCT scans, that normally cause the incident light to scatter, thus partially preventing deeper transmission of light (and therefore OCT signal) into the choroid. OCT allows cross-sectional visualization that permits image readers to characterize microstructural alterations in the different laminae of the retina. Using only one type of scan for documenting both en face and cross-sectional images of the retina, it can therefore provide more detailed insight in retinal alterations of GA patients than fundus autofluorescence imaging.

However, there are a number of problems with current techniques for quantifying GA. For example, techniques that rely on simple signal integration only indirectly address the physical phenomenon of decreased attenuation that is actually occurring. Similarly, techniques based on signal integration are subject to multiple types of signal shadowing: (1) beneath retinal blood vessel locations (though vessel sizes tend to be small in the macula); and (2) from cataracts, in which entire areas could be affected. Such methods also utilize spectral domain OCT (SD-OCT) with an 800 nm wavelength. It should be noted that 800 nm light is significantly more affected by cataracts than light with longer wavelengths. The intensity of signal that is significantly attenuated (e.g., 800 nm signal in the choroid or sclera) can be artificially elevated by the OCT system's noise floor. As a technique, this will serve to increase measurement variability and reduce methodological sensitivity/specificity. For the sub-RPE slab technique, the complexity of the OCT signal in the choroid can lead to some degree of randomness in the integrated signal and resulting analysis. The inner choroid, including the choriocapillaris and Sattler's layer, includes many high intensity pixels, but with great variation both in intensity and spatially. The outer choroid, consisting of Haller's layer, comprises many pixels of lower intensity corresponding to large blood vessels, but the size (both in terms of width and thickness) and spacing of such vessels can vary widely. Meanwhile, full OFI techniques (signal summation over a full A-line) are subject to noises related to inner retinal signals that are completely independent of AMD phenotypes. These deficiencies can produce complexities that make it difficult for image processing algorithms to effectively and robustly detect atrophic regions.

In addition to the above, ANSI, and possibly other standards organizations as well, places safety limits on the maximum power density that can be applied to the ocular surfaces such as the cornea and retina. This means that there is an effective limit with respect to the achievable sensitivity for in vivo ocular imaging. With this in mind, it is not possible to arbitrarily increase the light power in order to achieve any desired signal intensity at deeper retinal positions.

BRIEF SUMMARY OF THE INVENTION

Accordingly, a method of processing ophthalmic image data for detecting geographical atrophy is desired that overcomes the above limitations and deficiencies of the current systems and methods.

According to one example, a method of processing ophthalmic image data comprises obtaining optical coherence tomography (OCT) data of a subject's eye, the OCT data including data beyond the retinal pigment epithelium (RPE) of a subject's eye and intensities of an imaging signal as the imaging signal is backscattered by each of a plurality of tissue layers in the subject's eye; determining a ratio of the intensities of the backscattered imaging signal, the ratio being the intensity of a first portion of the backscattered imaging signal corresponding to at least a portion of a retinal layer with respect to the intensity of a second portion of the backscattered imaging signal corresponding to at least a portion of a sub-RPE layer; determining a representative value based at least in part on the determined ratio; and phenotyping or classifying the subject based at least in part on the determined representative value.

In various embodiments of the above example, the OCT data is captured at a plurality of times, a ratio and representative value are determined for the OCT data captured at each of the plurality of times, and the subject is phenotyped or classified based at least in part on a change in the determined ratios and/or representative values at the plurality of times; the change in the representative values and/or ratios is determined by performing a statistical measurement between the representative values and/or ratios at a first time of the plurality of times and the representative values and/or ratios and a second time of the plurality of times; the representative values and/or ratios at a first time of the plurality of times are registered with representative values and/or ratios at a second time of the plurality of times; the subject is phenotyped or classified based at least in part on detecting spot-like regions or statistical anomalies in representative values and/or ratios determined for OCT data obtained for a plurality of axial scans; the spot-like regions are determined by comparing spatial standard deviations or pattern deviations to a threshold level; the method further comprises applying a curve fitting technique to model a boundary traversing the bottom of the RPE based on pixels determined to correspond to the RPE, and selecting the sub-RPE region based at least in part on the smooth boundary; the representative value is selected from the group consisting of: attenuation coefficients, integrated attenuation, or a monotonic or near-monotonic proxy measurement; the method further comprises identifying diseased areas of the subject's eye based at least in part on the determined ratio or representative values; the method further comprises: identifying regions of the subject's eye based at least in part on a change in the determined ratios and/or representative values at the plurality of times; the imaging signal has a center wavelength of at least 1 μm; and/or the retinal layer, portion of the retinal layer, combination of retinal layers, sub-RPE layer, portion of a sub-RPE layer, or combination of sub-RPE layers is determined using polarization sensitive optical coherence tomography (PS-OCT).

According to another example, a method of processing ophthalmic image data comprises obtaining optical coherence tomography (OCT) data of a subject's eye for each of a plurality of axial scans, the OCT data including data beyond the retinal pigment epithelium (RPE) of a subject's eye and intensities of an imaging signal as the imaging signal is backscattered by each of a plurality of tissue layers in the subject's eye; determining a ratio of the intensities of the backscattered imaging signal, the ratio being the intensity of a first portion of the backscattered imaging signal corresponding to at least a portion of a retinal layer with respect to the intensity of a second portion of the backscattered imaging signal corresponding to at least a portion of a sub-RPE layer, for each of the plurality of axial scans; determining a representative value based at least in part on the determined ratio for each of the plurality of axial scans; generating a map of the representative values, ratios, the intensities of the first portion of the backscattered imaging signal, or the intensities of the second portion of the backscattered imaging signal; and phenotyping or classifying the subject based at least in part on the generated map.

In various embodiments of the above example, the OCT data is captured at a plurality of times, the map is generated for the OCT data captured at each of the plurality of times, and the subject is phenotyped or classified based at least in part on a change in the generated maps at the plurality of times; the change in the generated maps is determined by performing a statistical measurement between the representative values, ratios, intensities of the first portion, and/or intensities of the second portion at a first time of the plurality of times and the representative values and/or ratios and a second time of the plurality of times; the generated map at a first time of the plurality of times is registered with a generated map at a second time of the plurality of times; the subject is phenotyped or classified based at least in part on detecting spot-like regions or statistical anomalies in the generated maps; the spot-like regions are determined by comparing spatial standard deviations or pattern deviations to a threshold level; the method further comprises applying a curve fitting technique to model a boundary traversing the bottom of the RPE based on pixels determined to correspond to the RPE, and selecting the sub-RPE region based at least in part on the smooth boundary; the representative value is selected from the group consisting of: attenuation coefficients, integrated attenuation, or a monotonic or near-monotonic proxy measurement; the method further comprises: identifying diseased areas of the subject's eye based at least in part on the generated map; the method further comprises: identifying regions of the subject's eye based at least in part on changes between the generated maps at the plurality of times; the step of identifying diseased areas of the subject's eye further comprises: generating seeds of diseased areas, removing outliers of the generated seeds, growing a region encompassed by the generated seeds that were not removed, refining a contour of the grown regions, identifying an area inside the contour as diseased, and outputting the generated map with a contour around the regions identified as diseased or outputting a binary mask of the regions identified as diseased; the step of generating the seeds of diseased areas is performed by removing noise from the generated map and applying a thresholding technique on the generated map; the thresholding technique comprises finding an Otsu threshold of the generated map, comparing the Otsu threshold with a pre-set value, and selecting an intensity threshold based on the comparison, wherein the seeds of diseased areas are generated using pixels of the map that have intensities lower than the selected intensity threshold; the step of removing outliers is performed by grouping connected seed components and applying a distance analysis on the generated seeds; the imaging signal has a center wavelength of at least 1 µm; and/or the retinal layer, portion of the retinal layer, combination of retinal layers, sub-RPE layer, portion of a sub-RPE layer, or combination of sub-RPE layers is determined using polarization sensitive optical coherence tomography (PS-OCT).

BRIEF DESCRIPTION OF SEVERAL VIEWS OF THE DRAWING

FIG. 2B illustrates a B-scan corresponding to a cross section of the map of FIG. 2A through a section containing geographic atrophy;

FIG. 5A illustrates a flow chart of the seed generation steps of the method of FIG. 4;

FIG. 8A illustrates a contour of GA on the ratio map;

FIG. 8B illustrates the corresponding GA mask;

DETAILED DESCRIPTION OF THE INVENTION

Figure 1:
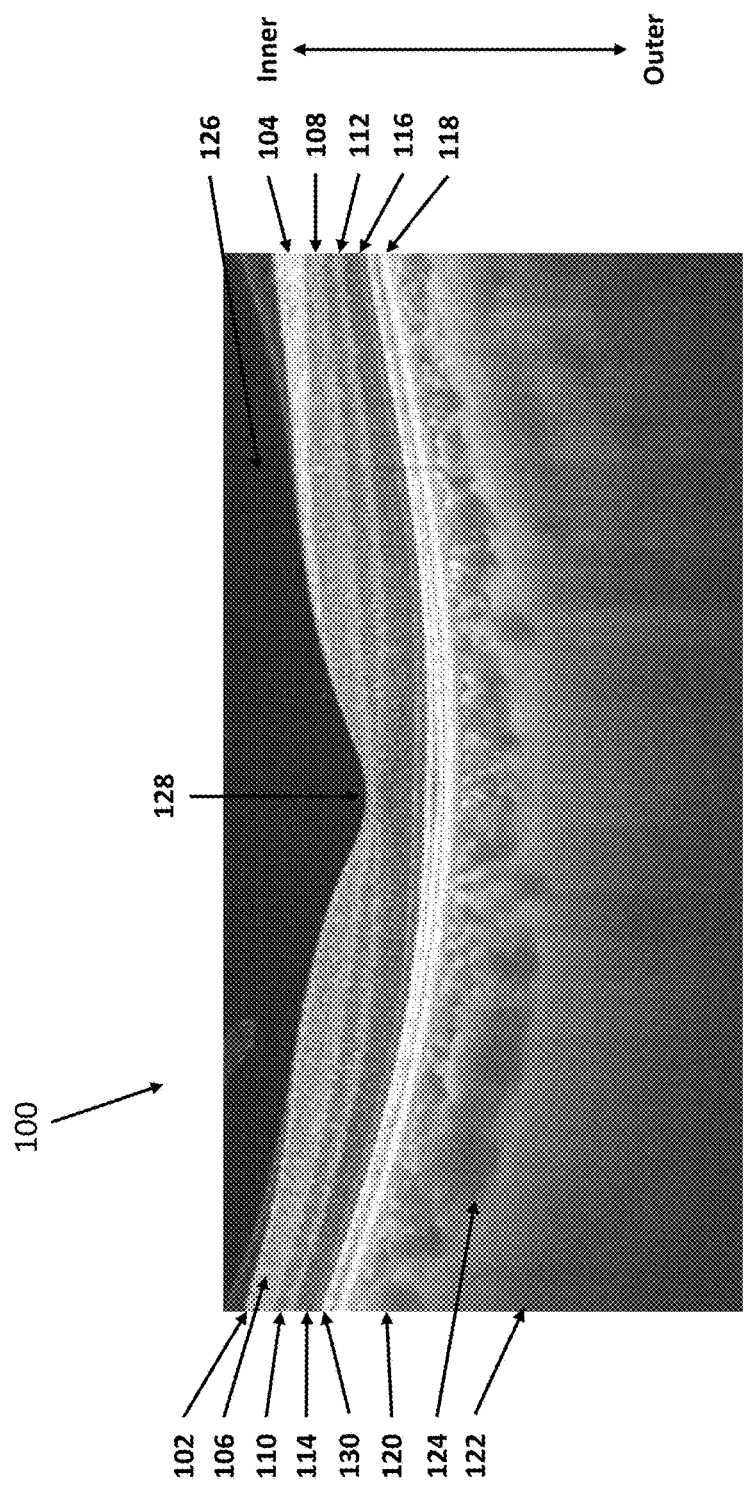
FIG. 1 illustrates the anatomy of the eye as referred to herein.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It should be noted that while this disclosure is based on the OCT imaging modality, it is not limited to OCT. For example, it is applicable to ultrasound as well. It should also be noted that the term "retina" typically refers to the tissue inner to the retinal pigment epithelium (RPE) cell bodies. For the purposes of this disclosure, the retina is defined as the tissue layers including and inner to the RPE cell bodies. Therefore, the choroid and sclera are not considered retinal tissue as used herein. A more detailed illustration of the anatomy and relative locations of layers of the eye and retina as referred to herein is shown in FIG. 1 on a typical OCT cross-sectional image (B-scan) 100. FIG. 1 illustrates the Inner Limiting Membrane 102, Nerve Fiber Layer (NFL) 104, Ganglion Cell Layer (GCL) 106, Inner Plexiform Layer (IPL) 108, Inner Nuclear Layer (INL) 110, Outer Plexiform Layer (OPL) 112, Outer Nuclear Layer (ONL) 114, External Limiting Membrane (ELM) 116, Retinal Pigmented Epithelium (RPE) 118, Choroid (120), Sclera 122, and Chorioscleral Interface (CSI) 124. The Vitreous and Foveal Pit are also shown. With further reference to FIG. 1, the Inner Segments (IS) range roughly between the ELM 116 and the Inner Segment Ellipsoids (ISe, also known as the IS/OS junction) 130. The Outer Segments (OS) are roughly between the ISe and Retinal Pigment Epithelium (RPE) 118. The Bruch's Membrane (BM) is generally estimated to be collocated with or immediately outer to the outer edge of the RPE 118. The choriocapillaris is too small to be imaged, but is immediately adjacent to and outer to the BM. The Cone Outer Segment Tips (COST) is shown towards the center of the scan between the ISe and the RPE.

Most commercial OCT equipment for retinal imaging to date has utilized light in the 800 nm band. However, 1 µm wavelength systems provide benefits in both research and commercial applications. Furthermore, swept-source OCT (SS-OCT) systems have an additional advantage over SD-OCT in that the signal rolloff characteristics are improved such that less relative loss is incurred at deeper depths within an image. 4096-pixel or other sized (e.g., greater than 2048 pixels) CCD cameras in SD-OCT can exhibit similar advantages of reduced signal rolloff characteristics. Using these systems, the imaging capabilities of the choroid is improved. Additionally, the outer choroid is typically visible (i.e., above the level of system noise) even in cases of very thick choroids, whereas traditionally this has often not been possible. Furthermore, particularly with the 1 µm wavelength (and especially in the case of a 1 µm SS-OCT system), the inner portions of the sclera—and sometimes its entirety—can often be successfully imaged.

Modern 1 µm OCT systems can achieve even better depth penetration (e.g., choroidal and scleral imaging capability), for example, by: (1) optimizing the center wavelength (e.g., slightly above 1040 nm); utilizing SS-OCT rather than SD-OCT, where SS-OCT has an improved SNR rolloff profile; and utilizing a CCD camera with a higher sensor count (e.g., 4096 sensors or pixels) in an SD-OCT system. Additionally, 1 µm light exhibits better penetration through cataracts than 800 nm light. An 800 nm system is more likely to exhibit attenuation and/or shadowing in A-lines affected by cataracts. 1 µm light, as it is in the infrared range, is invisible to the patient. This reduces the degree of stimulation to the eye during a scan, and may lead to reduced eye motion in the captured OCT data. Therefore, the captured 3D OCT data itself may be of higher fidelity, potentially leading to fewer side effects in the subsequent image processing operations. Additionally, 800 nm SD-OCT exhibits greater retinal signal attenuation than 1 µm SS-OCT. For example, this attenuation can be about 5-10 dB at depths at and beyond the RPE.

Polarization sensitive OCT (PS-OCT) is an OCT technique that takes advantage of changes to a light's polarization state that has occurred in the tissue being imaged. During PS-OCT, a light source is polarized in the reference and probe arms of the OCT system. The backscattered light can then be detected in two orthogonal polarization channels to detect changes in polarity between the source light and the backscattered light. This technique is particularly useful in retinal imaging because the retina contains both birefringent and depolarizing tissues. Thus, PS-OCT offers increased sensitivity for differentiating between various retinal layers.

Furthermore, it should also be noted that while the methodology disclosed herein is by no means limited to 1 µm wavelength and/or SS-OCT systems (and/or SD-OCT 4096-pixel or other sized CCDs) or PS-OCT, its robustness can be enhanced by the improved imaging penetration depth associated with such technologies. These enhancements, for example, make possible the relatively reliable use of the choroid/sclera interface (CSI) boundary and/or scleral signal integrations. For example, the disclosed methodology may be applicable to 800 nm OCT systems, including spectral domain OCT (SD-OCT), swept-source OCT (SS-OCT), and PS-OCT.

The present disclosure is also applicable towards a scan of any suitable dimension. For example, traditional 6 mm by 6 mm and wide scan protocols such as 12 mm by 9 mm, as well as scans of arbitrary dimensions, are envisioned to be within the scope of the present disclosure. Two-dimensional (2D) and three-dimensional (3D) scans of various dimensions are also envisioned. Accordingly, the use of particular scan dimensions in the present disclosure is not intended to represent limiting embodiments.

In one or more aspects described herein, systems and methods for atrophy identification, measurement, and/or visualization of regions of reduced tissue attenuation are based on either: (1) a ratio of integrated signals; or (2) a ratio-less signal integration. In one embodiment, this aspect can be used in conjunction with 3D OCT scans for the diagnosis, monitoring, and/or treatment of GA. However, this aspect of the invention is also applicable to other diseases with atrophy that are detectable via attenuation-related analysis, and via modalities other than OCT (e.g., ultrasound).

The aspects described herein can be used to determine and/or measure one or more of the following: (1) which locations specifically are diseased; (2) the area of individual, disease affected regions; (3) the number of individual, disease affected regions; (4) the total area of disease affected regions; (5) the circumference of individual disease affected regions, and (6) the total circumference of disease affected regions. This data, and more generally the aspects described herein could also be used on subjects who have not yet shown any symptoms of GA, including healthy subjects and those who are in early-to-mid stages of AMD (before late stage symptoms such as GA). This data and the aspects described herein could be used to determine and/or measure such data, can be used for monitoring and diagnostic purposes at a single time or over a period of time.

Furthermore, because ratios of integrated signals themselves objectively represent a physically meaningful phenomenon related to attenuation, the ratios may be a useful indicator and/or predictor of GA (or AMD in general) both in areas of complete atrophy and in surrounding regions. Relative differences between ratios in nearby areas might be similarly useful. As these ratios can be used as an objective measure of physical tissue characteristics, they may be useful towards both identifying atrophic regions via post-processing of ratio maps, and quantifying RPE integrity spatially over the scan area.

In one embodiment related to the ratio of integrated signals, the ratio could be based on signal integration of the retinal signal versus the choroidal and/or scleral signal for determining GA. It should be noted that the layer combinations could vary for other modalities and other diseases, without varying from the scope of the present invention. In other embodiments, the signal integration (i.e., the ratio-less) methodology could correspond to a fixed-depth integration. For example, the inner border of the depth to be integrated could correspond to either at or outer to the Bruch's membrane or the distal boundary of the RPE cell bodies when the Bruch's membrane itself cannot be resolved. Again various layers, parts of layers, and combinations of layers could be used without deviating from the scope of the present invention.

The inner retinal layers are used in the ratio based aspect and, as used herein, are defined as any of: (1) the RPE itself; (2) the inner limiting membrane (ILM) to the Bruch's membrane boundaries; (3) the NFL/GCL to the Bruch's membrane boundaries; (4) the outer plexiform layer OPL/ outer nuclear layer (ONL) to the Bruch's membrane boundaries; (5) a fixed depth thick layer where the inner border of the fixed depth to be integrated could correspond to either at or outer to the Bruch's membrane or the distal boundary of the RPE cell bodies when the Bruch's membrane itself cannot be resolved; or (6) any combination of retinal layers. The outer retinal layers are used in both the ratio and ratio-less based aspects and, as used herein, can include all or portions of the choroid and/or sclera. For example, this means that the outer retinal layers could include only the inner portion of the choroid (e.g., ignoring the Haller's layer). In some embodiments, when using only a scleral signal, it might be beneficial to ignore feeder vessels.

The sclera has a more uniform signal distribution than the choroid (which has three major sublayers and is additionally highly varied spatially due to dynamic blood vessel morphologies); although because the sclera contains some degree of feeder vessels, it may sometimes yield a less uniform signal. This represents a relative advantage for the sclera. However, due to equipment sensitivity considerations, the choroid (and particularly its inner portion) may be more practical. Segmentation accuracy of the Bruch's membrane/choroid boundary versus the CSI is another practical consideration.

Segmentation of intensity-only images (e.g., traditional B-scan OCT images) can often contain errors in atrophic regions because it is difficult for layer detection algorithms to differentiate between healthy tissue (e.g., the RPE) and extracellular material that might resemble the healthy tissue (e.g., the atrophic regions). As mentioned above, the use of PS-OCT systems can provide increased sensitivity in this regard. For example, in GA, PS-OCT indicates that the RPE is not continuous despite a bright signal corresponding to laminar deposits on the Bruch's Membrane that is frequently visible in structural OCT images and can often be mistaken as RPE signal. Accordingly, PS-OCT can be helpful in assisting the attenuation-based image processing such that the RPE signal (inner map) can be accurately limited to the RPE itself, and/or can be utilized directly to indicate atrophic areas. With PS-OCT, healthy tissue layers can be better identified using the derived characteristic degree of polarization uniformity (DOPU) and a thresholding methodology. For example, the DOPU for identifying and segmenting the RPE can be found by first calculating the Stokes vector S on a pixel-by-pixel basis according to:

$$S = \begin{pmatrix} I \\ Q \\ U \\ V \end{pmatrix} = \begin{bmatrix} A_x^2 + A_y^2 \\ A_x^2 - A_y^2 \\ 2A_x A_y \cos\Delta\emptyset \\ 2A_x A_y \sin\Delta\emptyset \end{bmatrix}$$

Then, the DOPU may be calculated according to:

$$DOPU = \sqrt{Q_m^2 + U_m^2 + V_m^2}$$

Finally, the RPE may then be identified by segmenting out pixels with DOPU levels below a predetermined threshold, for example, 0.65. Furthermore, based on the pixels determined to correspond to the RPE, a curve fitting technique may be applied to model a boundary traversing the bottom (outer edge) of the RPE or other arbitrary part of the RPE as desired. This fitted boundary may serve as the Bruch's Membrane boundary for selecting the sub-RPE region.

For simplicity, the following disclosure describes pixel intensity integrations as a fixed-depth integration (such that integration occurs over a fixed number of pixels, corresponding to a constant depth) for the outer layer calculation. However, it should be noted that for the outer reference layer, it is mathematically equivalent to take either the sum over a fixed depth or to take the mean pixel intensity over either a fixed or variable depth. Calculating over a variable depth may involve making a modeling approximation, but the calculation results can still be expected to convey physical meaning. Averaging over a variable depth may allow the calculation methodology to increase the degree of averaging (i.e., include more pixels in the mean calculation), which can serve to reduce the effects of Gaussian and/or speckle noise. Therefore, even though it may not be ideal from a physical equation point of view, the reduction in noise may outweigh physical concerns. Furthermore, other calculation schemes could be both practical and beneficial, considering the complex nature of choroidal signal in OCT images. For example, taking the maximum intensity projection or an average of the n maximum values within a region of interest might in some circumstances yield more consistent image processing results than simple integrations. Likewise, taking the median or some arbitrary quantile of the pixel signal intensity levels could also be performed. Similar variations to the inner layer combination calculations can be performed. For example, instead of integrating the signal, the mean pixel value can be calculated. It should be noted that if the inner layer calculation depth were to vary from A-scan to A-scan, this might reduce the accuracy of the ratio's physical meaning, but the calculation results could still be a useful towards identifying regions of geographic atrophy.

In one or more embodiments, the calculation of a ratio of signal intensities of backscattered light (one part of the ratio representing a reference layer) is a key component of an attenuation calculation for determining atrophy. The ratio of a mean or integrated signal intensities calculation result could be directly utilized as a proxy indicator for integrated attenuation itself. Although integration over a fixed depth may better correspond to the physical equations, the mean calculation typically will also work well.

Rather than taking the ratio of a mean or integrated signal, individual ratios may be found for combinations of intensities of backscattered light from the inner retinal layers and outer retinal layers in an A-line in order to estimate the ratio value. For example, using a fixed-depth across all A-scans for each of the inner and outer regions, individual ratios may be found for pixel intensities at corresponding depths. The individual ratios may then be combined by taking the sum, mean, median, quantile or other similar statistical function. Another similar method envisioned involves calculating a ratio for every combination of pixels in the inner and outer regions. The sum of every ratio for each pixel in the outer region can then be calculated to find a single ratio value for each outer region pixel. Finally, the sum, mean, median, or similar statistical function can be calculated for each of the single ratio values, which can optionally be scaled by a desired constant. That is, for example, $R = \Sigma_{x=1}^{d1} \Sigma_{n=1}^{d2} (Ti_n / To_x)$, where x and n represent pixel locations with depths d1 and d2 for the inner and outer regions, respectively, and Ti and To represent the intensities of the inner region pixels and outer region pixels, respectively, within a given A-scan. In this way, the depths corresponding to the inner and outer regions may be different. With small variations to the preceding equation, the depths d1 and/or d2 may even vary from A-scan to A-scan.

An attenuation coefficient in units of inverse distance (e.g., mm$^{-1}$) can be determined according to:

$$\mu_{ATT} = \frac{\log(R/\beta + 1)}{2d}$$

where β is modeled as a constant value (subject to variation somewhat by subject, location, and layer) which can be estimated via empirical methods, R is the ratio value, $\mu_{ATT}$ is the measurement value and represents a total attenuation of light over a depth d. This coefficient can be modified to find a unitless integrated attenuation measurement that is monotonic with respect to the ratio value and determined according to the following relation:

$$\mu_{ATT}d = \frac{\log(R/\beta + 1)}{2} \approx f(R)$$

where f(R) represents a monotonic function. Although β may be subject to some variation across a volume, on a relative localized basis monotonicity would still likely be preserved as long as such variation is relatively gradual. In some cases, d may be effectively kept constant by, for example, integrating over a fixed depth or taking the mean of the integration, which is mathematically equivalent to integrating over fixed depth except that another constant (such as β) would be made to reflect the induced scaling factor.

In the above, any sub-RPE signal may be used as a reference signal for determining the attenuation of the RPE. In this case, the ratio value is defined according to:

$$R = \frac{T_{RPE}}{T_{subRPE}} = \frac{\alpha_{RPE}(e^{2\mu_{RPE}d_{RPE}} - 1)}{\alpha_{subRPE}(1 - e^{-2\mu_{subRPE}d_{subRPE}})} = \beta(e^{2\mu_{RPE}d_{RPE}} - 1)$$

$$\text{and } \beta = \frac{\alpha_{RPE}}{\alpha_{subRPE}(1 - e^{-2\mu_{subRPE}d_{subRPE}})}$$

where T represents the total backscattered light of a layer or combination of layers and β is globally constant, given practical computational concerns.

These equations relate the aggregated RPE signal and an aggregated sub-RPE signal to arrive at the integrated attenuation of the RPE. On the RPE (inner) end, other layers and combination of layers can be used for both theoretical and practical reasons. In GA, for example, atrophy is actually more extensive than just the RPE, extending to the outer and inner segments, the outer nuclear layer, and the choriocapillaris. By including any such layers, they can be factored into the computations. In GA, atrophy can cause the RPE to degrade and virtually disappear. It may be computationally useful, therefore, to include additional tissue in the model with which to calculate attenuation-related parameters. It can be challenging to achieve highly accurate layer segmentation, especially for diseased retina, and especially with automated algorithms. Therefore, PS-OCT (as described above) may be used in embodiments where such situations arise. It is even possible to include all or most of the inner retinal layers and achieve reasonable results.

Therefore, in another embodiment, the above ratio value equation may be even more generalized according to:

$$R = \frac{T_{Retina}}{T_{subRPE}} = \frac{\alpha_{Retina}(e^{2\mu_{Retina}d_{Retina}} - 1)}{\alpha_{subRPE}(1 - e^{-2\mu_{subRPE}d_{subRPE}})} = \beta(e^{2\mu_{Retina}d_{Retina}} - 1)$$

$$\text{and } \beta = \frac{\alpha_{Retina}}{\alpha_{subRPE}(1 - e^{-2\mu_{subRPE}d_{subRPE}})}$$

Using this generalized model along with the above unitless integrated attenuation may be more usefully and flexibly applied because the calculated integrated attenuation values are dependent on one fewer variable (the inner tissue thickness). This form thus calculates the total integrated attenuation associated with the retina (or retinal layers or portions of retinal layers), with an effective emphasis on that of the RPE cell bodies.

It should also be noted that either prior to or as part of the signal intensity integrations, OCT image pixel intensity values can be calibrated or corrected based on signal rolloff characteristics (corresponding to light source and detection scheme, for example) or system noise floor characteristics. Furthermore, for embodiments related to the ratio of integrated signals, when the inner and outer layers or combinations of layers are not adjacent tissue, a calibration or correction factor may be introduced to represent any attenuation associated with intermediate layers that might not be included in the present attenuation model.

In one or more aspects described herein, the presumed monotonicity of the above equations enables relative comparison of ratio values across a given patient's ratio map of the scanned area. In other words, it enables image processing operations on 2D ratio maps that can be created. Additionally, inter-subject receiver-operating-characteristic (ROC) maps can be analyzed while still remaining within the scope of this invention.

In an example based on the preceding generalized equation, it can be inferred that those areas with very low integrated attenuation (which can then further be correlated to attenuation coefficients, if desired) correspond to those areas in which the ratio is very low and correspond to probable diseased areas, especially when such areas are clustered. Calculating the ratio over an entire map, therefore, combined with suitable post-processing, enables the detection of diseased regions.

Figure 2A:
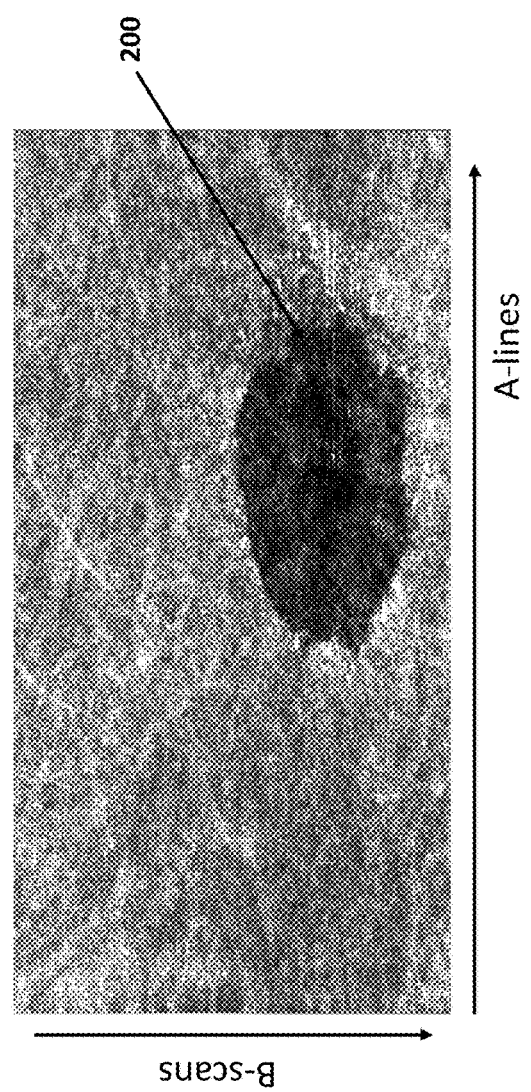
FIG. 2A illustrates one embodiment of a ratio map showing geographic atrophy.

The aforementioned maps are envisioned to be of attenuation coefficients, integrated attenuation, or a proxy measurement (such as a monotonic or near-monotonic transform) that provides sufficient sensitivity/specificity to detect locations of retinal atrophy. That is, in a 2D map, one axis of the map corresponds to A-lines of a B-scan and the other axis corresponds to the B-scans. The value at any given point represents one of the above measurements—that is, the value of an integrated layer(s), the determined ratio, the attenuation coefficient, the integrated attenuation, and the like. For purposes of this description, any such map will be referred to as a "ratio map". A sample ratio map and 2D B-scan corresponding to a cross section of the map through a section 200 containing GA are provided in FIGS. 2A and 2B, respectively. The inner retinal layer corresponds to a layer, portions of a layer, or combination of layers inner to (and possibly including) the RPE complex. Similarly, the outer layer corresponds to a layer, portions of a layer, or combination of layers outer to the RPE complex (e.g., choroid and/or sclera). It should also be noted that the ratio values may be transformed so as to bring them more in line with attenuation outputs, for example, dividing by an approximated constant β, adding 1 to that result, and/or then taking the log transform.

These maps, and the underlying data, may be indicative of phenotypes or disease classifications associated with the subject. For example, darker regions and more intensely shaded/brighter regions on the map would indicate a phenotypic feature; darker regions likely being atrophic. Furthermore, the areas and patterns of shading/darkness may be indicative of the direction atrophy is likely to spread in the future.

In other aspects, some type of thresholding is used to identify the atrophic disease regions in a ratio map. Such thresholding can be of any of type, including but not limited to: absolute levels—e.g., a ratio below a certain level always represents a disease condition; scan relative levels—values that are proportionately low within a scan represent a disease condition; and local relative levels—values that are proportionately low within a local region.

In still other aspects, image frame averaging OCT images is used to improve SNR in OCT images, while reducing the appearance of both Gaussian and speckle noise. Various averaging protocols, including but not limited to: in-place averaging—in which every B-scan is a composite image comprising an average of multiple single-frame B-scans; three-dimensional moving averaging—where each frame reflects a rolling average of spatially distinct frames; and whole-volume averaging can optionally be employed as a pre-processing operation to improve image quality.

Figure 3:
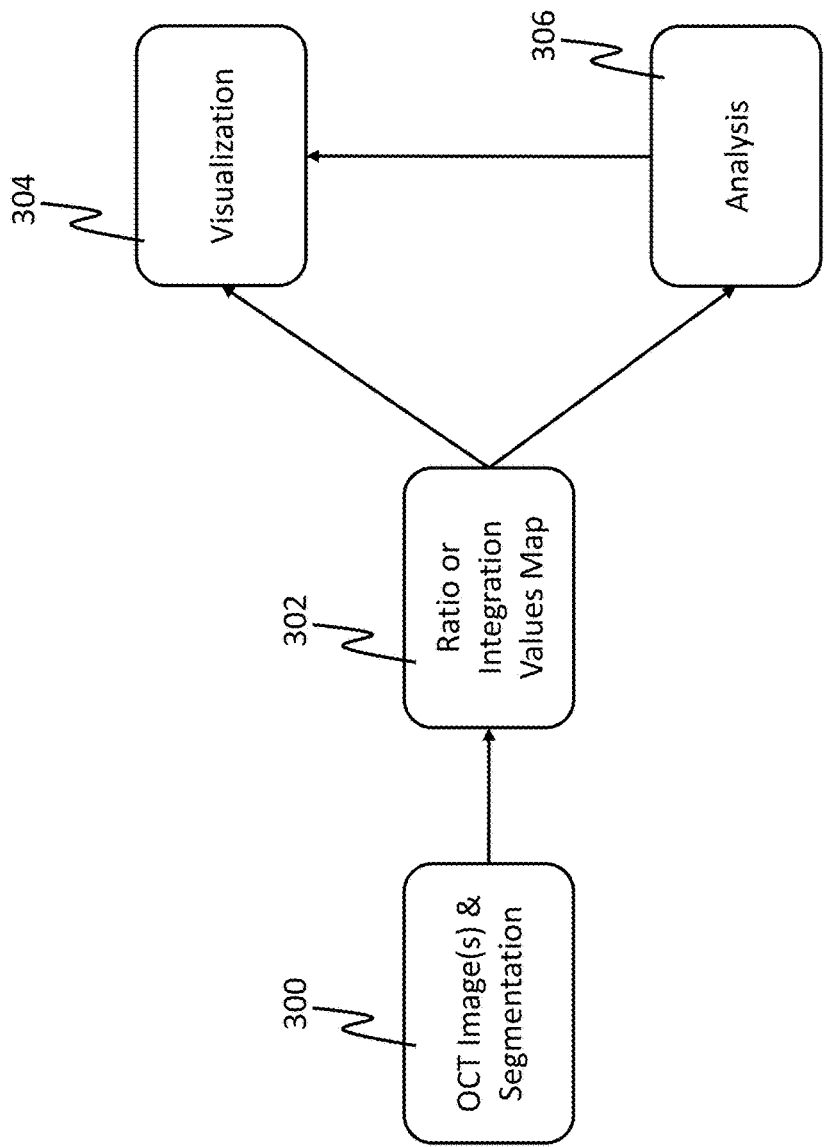
FIG. 3 illustrates one example of a general framework described herein to identify, measure, and/or visualize signal attenuation associated with atrophy.

One example of a general atrophy detection framework according to the above aspects and embodiments, as illustrated in FIG. 3, comprises a 2D ratio based map that is generated from a 3D OCT volume, including several image processing steps to identify the atrophic region contour.

FIG. 3 may apply to both 2D (e.g., single B-scan only) and 3D image embodiments. In step 300, OCT data is acquired from any OCT or like imaging machine (frequency domain OCT, time domain OCT etc.) that covers macular and/or optic disc regions and the data is segmented. Segmentation results may, for example, be boundary heights or layer region information covering a retinal and/or choroidal region. In step 302, a ratio or integration value map is calculated. Such a map can be any form of integration values of certain layers, distance measurements, ratios of integration values or distance measurements with respect to various layers, and the like, as previously discussed. Integration can be a summation, average, or other mathematical form within/across partial or full A-scans. The measurement can be based on image intensities, ideally in linear scale. The integrated or ratio value map can also be adjusted based on local characteristics (such as normalized by local mean and maximum values). Adjustments may include normalizing out the noise floor and/or sensitivity roll-off (estimated characteristic) on a row-by-row basis. Finally, step 304 comprises visualization, which can be 1D, 2D or even 3D depending on the desired map. An analysis in step 306 can be any image processing steps to extract the border/contour of a region of interest from the ratio based map/values. More detailed examples of image processing steps that are within the scope of analysis step 306 are shown in FIGS. 5-8 and explained in more detail below.

Figure 4:
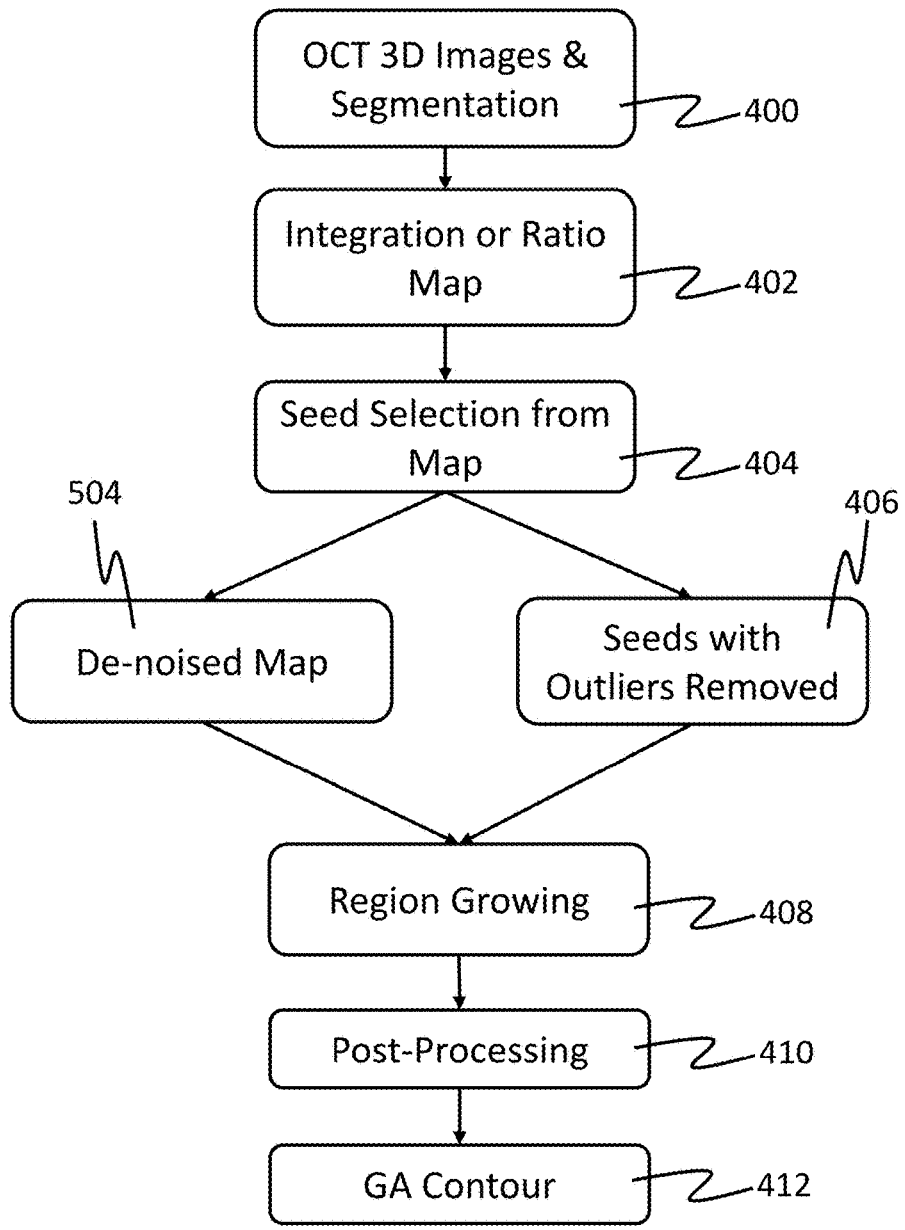
FIG. 4 illustrates a flow chart of one example of the method described herein to identify and/or measure signal attenuation associated with atrophy.

A more detailed example of a framework is illustrated in FIG. 4. The framework described above with respect to FIG. 3, and below with respect to FIG. 4, may be implemented automatically using a processor of the imaging device or an external device (e.g., an end user's computer). Following imaging and segmentation 400, an integration map (e.g., whereby the total intensity for each A-line is calculated) or a ratio map (e.g., with retinal signal versus choroidal or scleral signal for each A-line) as discussed above is generated 402. A ratio map can enhance GA features because the retinal signal will be weaker as a result of possible loss of RPE and/or outer segment (OS) while the choroidal signal will be increased with the absence of RPE.

Figure 5B:
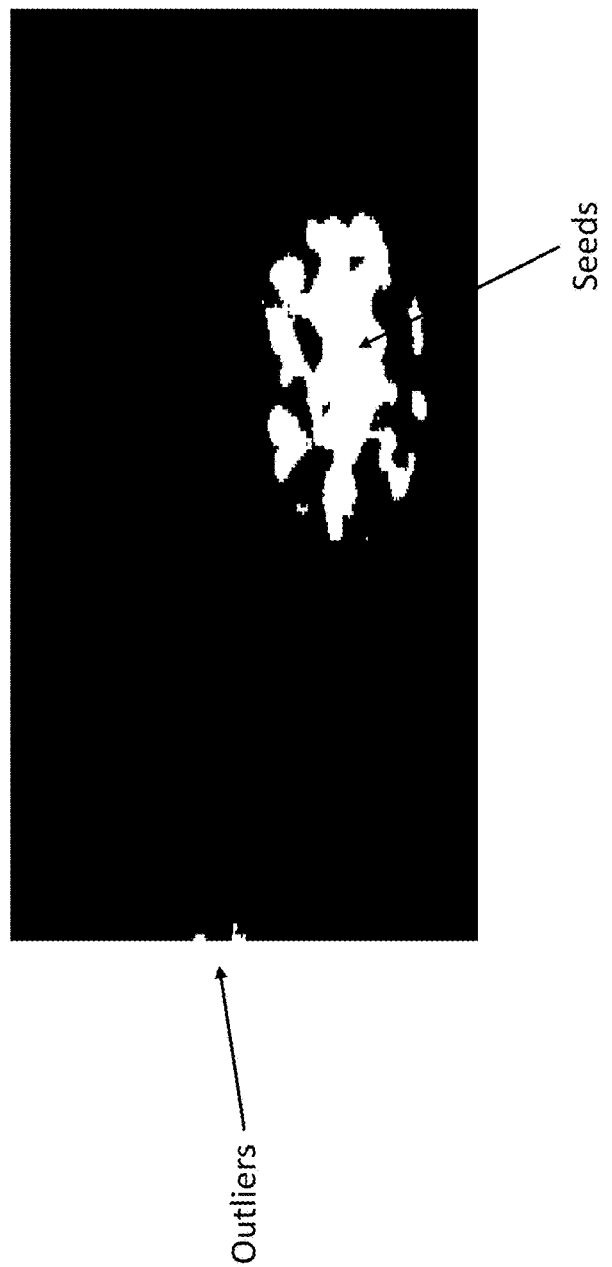
FIG. 5B illustrates the extracted seeds on the ratio map.

Next, seed selection 404, as shown in more detail in FIGS. 5A and 5B, is performed on a map 500 generated in step 402. Step 502, involving map normalization, is an optional step that can be achieved in various ways, such as histogram equalization, image adjustment by saturating certain percentage of low and high intensities, or normalization by a reference map. Map de-noising in step 504 includes but is not limited to the following image enhancement techniques: Gaussian smoothing filter, median filter, anisotropic diffusion filter, wavelet de-noising filter, morphological filters, subtracting background noise, order statistic filtering, and removing blood vessel artifacts.

Figure 5C:
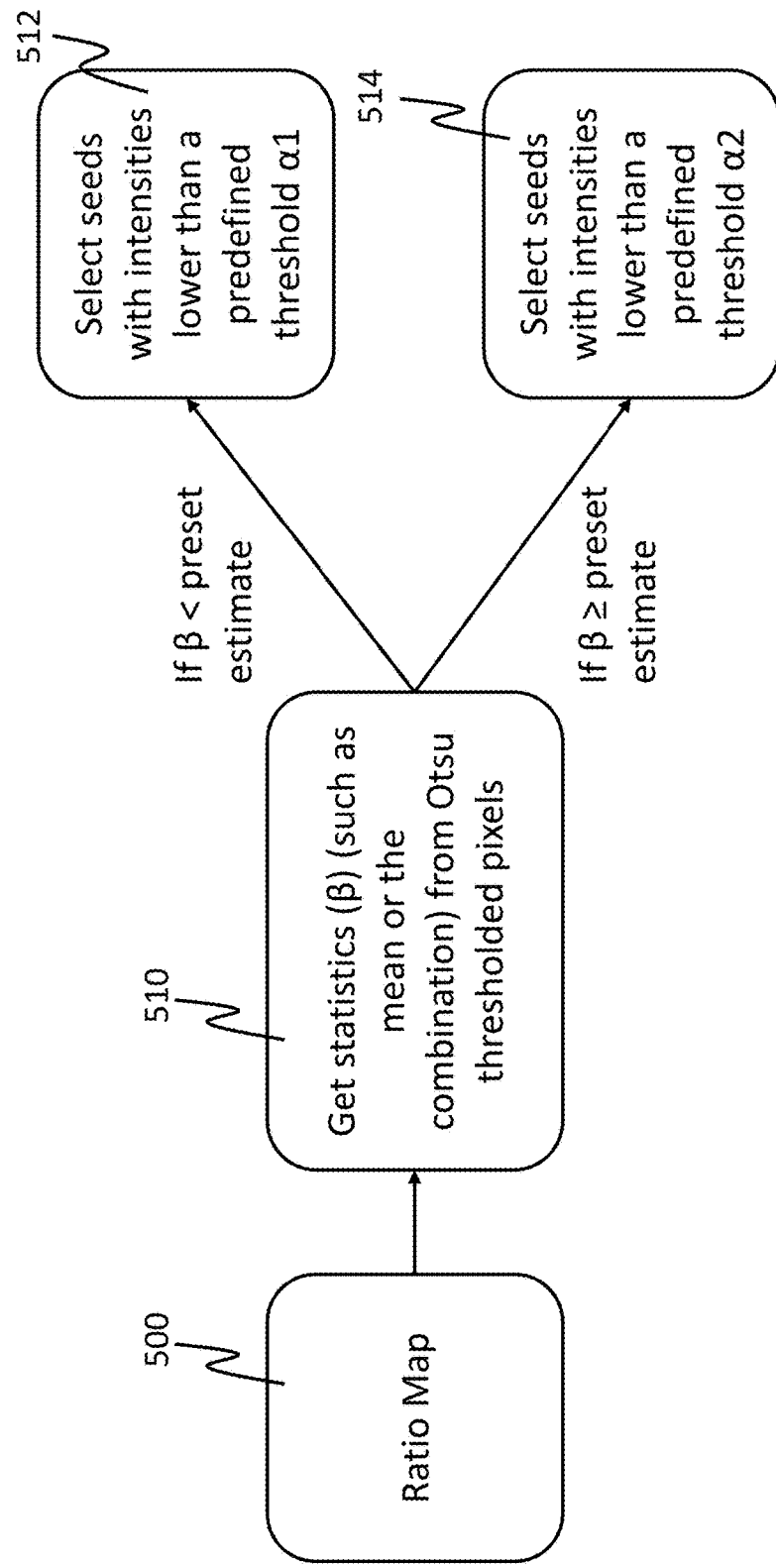
FIG. 5C illustrates a flow chart of an example of a flexible thresholding technique based on Otsu's method.

Map thresholding of step 506 is used to generate extracted seeds 508, as shown in FIG. 5B (including outliers) by applying a desired threshold to the de-noised map. When the ratio map normalization step is bypassed, the thresholding step applies absolute, rather than relative, thresholds. These absolute thresholds can result in greater sensitivity and specificity than relative thresholds based on a normalized ratio map. It has also been found that a total or partial RPE atrophy can be accompanied with extracellular deposits above the Bruch's Membrane, which is commonly seen in unifocal cases. These extracellular deposits can impact attenuation in different ways than the RPE itself. Thus, one threshold level may not work best for every situation. Optionally, an adaptive method (e.g., based on an Otsu's pixel clustering method) for customizing the seeding threshold level can identify characteristics associated with the above mentioned unifocal cases, for example. The adaptive method can be based on various other thresholding techniques such as entropy based threshold technique, other thresholding techniques including using a fixed value, statistics (such as mean, median, maximum, minimum, and the like), and combinations thereof. An example of a flexible thresholding technique based on Otsu's method is illustrated in FIG. 5C. In step 510, the ratio map 500 is used to obtain the Otsu threshold ($\alpha$) and statistics ($\beta$), such as the mean, from the pixels that have a lower intensity than the Otsu threshold. Next, if the statistics $\beta$ are lower than a preset estimate, seeds are generated using pixels that have intensities lower than a first threshold $\alpha 1$ in step 512; if either statistics $\beta$ are greater than or equal to the preset estimate, seeds are generated using pixels that have intensities lower than a second threshold $\alpha 2$ in step 514.

Figure 6A:
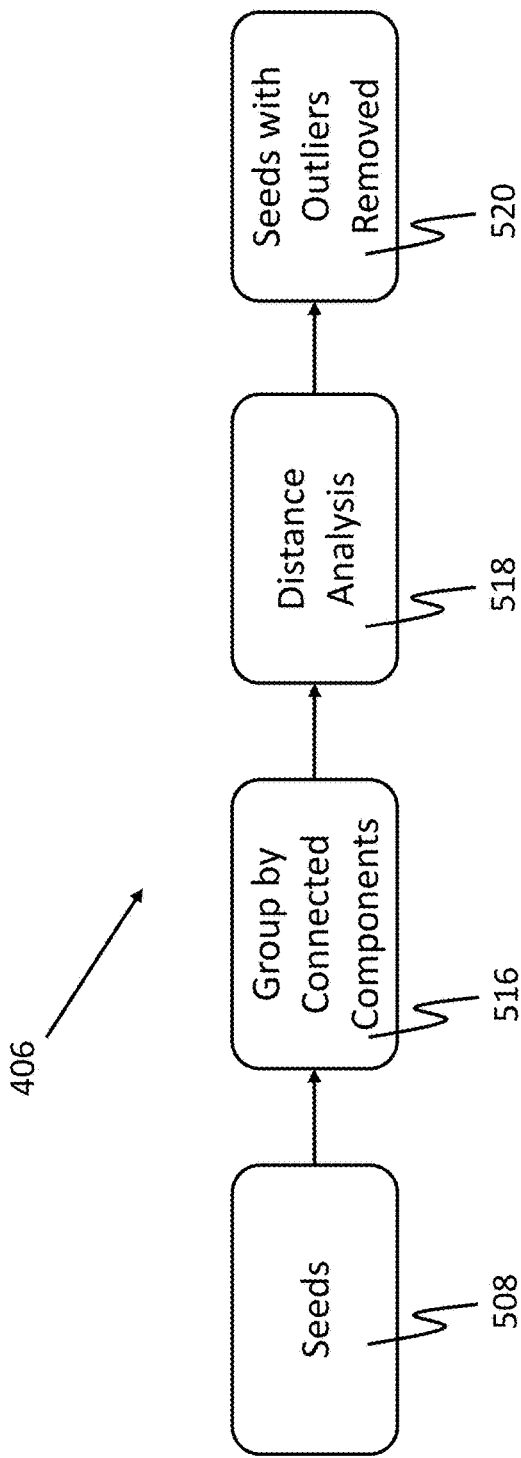
FIG. 6A illustrates a flow chart of the seed refinement steps of the method of FIG. 4.
Figure 6B:
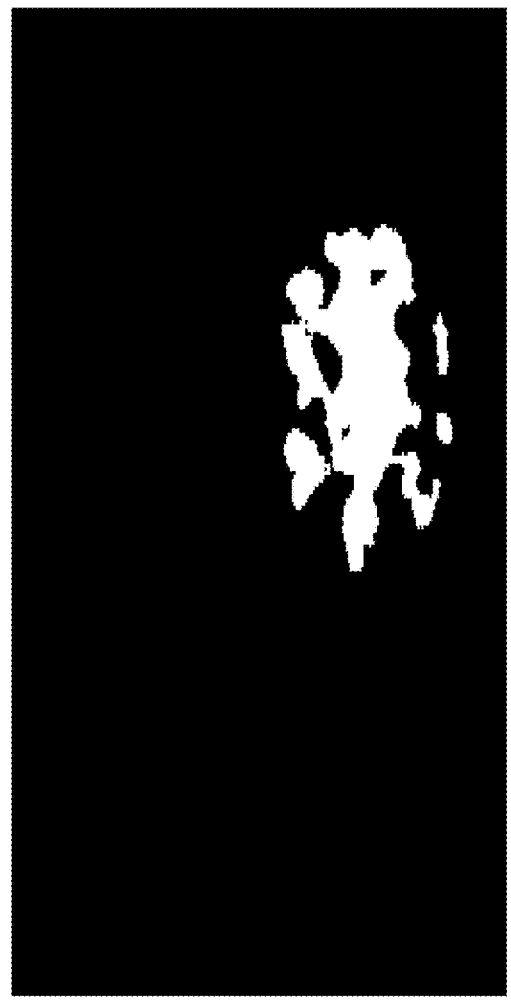
FIG. 6B illustrates the extracted seeds with the outliers removed.

Next, the extracted seeds may be refined, for example by removing outliers 406, as shown in FIGS. 6A and 6B. In step 516, seeds 508 are grouped by connected components. Step 518 employs a distance analysis: the absolute center locations of each component and/or the absolute Euclidean distance from each component to the fovea and/or the relative Euclidean distance between components are analyzed to remove the outliers 520. The criteria to remove the outliers can be a simple distance thresholding, a heuristic based on the statistical analysis of the distances (such as mean and standard deviation) combined with the pixel numbers of the components, cluster analysis, or various other similar techniques. Again, the extracted seeds are shown on the ratio map in FIG. 6B, however, the outliers have been removed.

Figure 7:
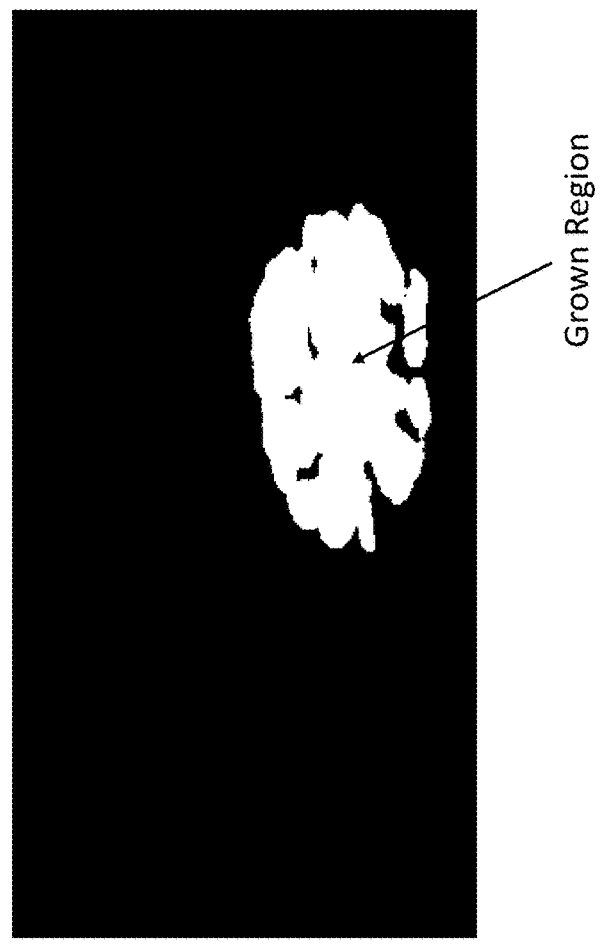
FIG. 7 illustrates region growing results.

Next, the de-noised map 504 and seeds with outliers removed 406 are used to grow the seed region in step 408. The region growing step 408 can be performed separately on each connected component seed or just the seeds from one component. The mean, standard deviation, gradient information, and/or other statistical descriptors may be used in a single iteration or multiple iterations to grow the seed region. Region growing 408 may also include post-processing such as hole-filling or convex hull operations. Results of such techniques are shown in FIG. 7, illustrating that the area of the seeds with respect to FIGS. 5B and 6B has increased.

Finally, the results of post processing 410 and contouring 412 are shown in more detail in FIGS. 8A and 8B. During the contouring step 412, a contour around the grown seeds is provided and may be output as a binary mask or in a similar visualization—that is, the area contained within the contour may be specially designated (e.g., white) to indicate a region of geographic atrophy, while the remaining area of the image is designated, for example, black. Such a mask is illustrated in FIG. 8B while the contour is illustrated on the original cross-sectional image in FIG. 8A. A contour may be refined by smoothing (e.g., using a moving average) or re-detecting contours for each component with guidance from the original contour. Such guidance could include using a graph search to re-search the contour based on the image contrast. The overall image processing and analysis is not limited to the region growing method. Any segmentation method, such as active contour based segmentation or watershed segmentation, that creates similar results as shown herein are envisioned within the scope of the present disclosure.

Figure 9A:
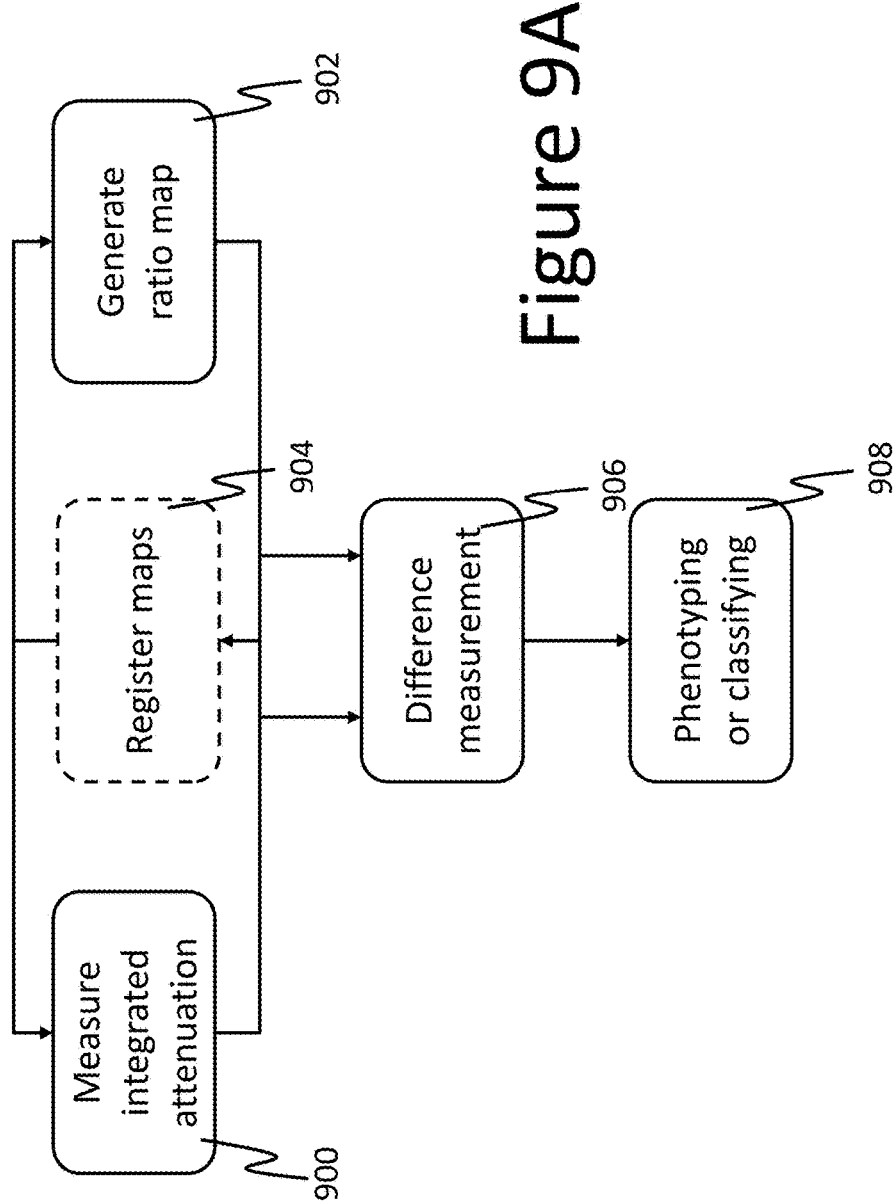
FIG. 9A illustrates a method of monitoring disease progression over a period of time.

An example method for using the above-described aspects for monitoring disease progression (over a period of time) of AMD (including on subjects who have not yet shown any symptoms of GA and/or are in early-to-mid stages of AMD before late stage symptoms such as GA) is illustrated with respect to FIG. 9A. A first step may include measuring integrated attenuation 900 and/or generating a ratio map 902 over some frequency of time (e.g., every few months, 6 months, or 1 year; regularly or irregularly), for example, by scanning a subject's eye at each of the intervals to generate a plurality of sets of data. In some embodiments, the ratio maps for each measurement may be registered 904 to one another. Then, progression may be detected by applying a difference measurement 906 from one measurement period to the next (or any arbitrarily later period). Put another way, relative changes of regions of interest may be monitored between measurements at different times. The difference calculation itself could be a range of operations, for example, subtraction, division, or any other statistical measurement for determining differences between sets of data. This progression information may also be used for phenotyping or classifying 908 the subject, for example, with respect to RPE integrity. Additionally or alternatively, such a phenotyping may include a disease classification and/or a rate of change that could be associated with, for example, certain physiological conditions or diseases.

Figure 9B:
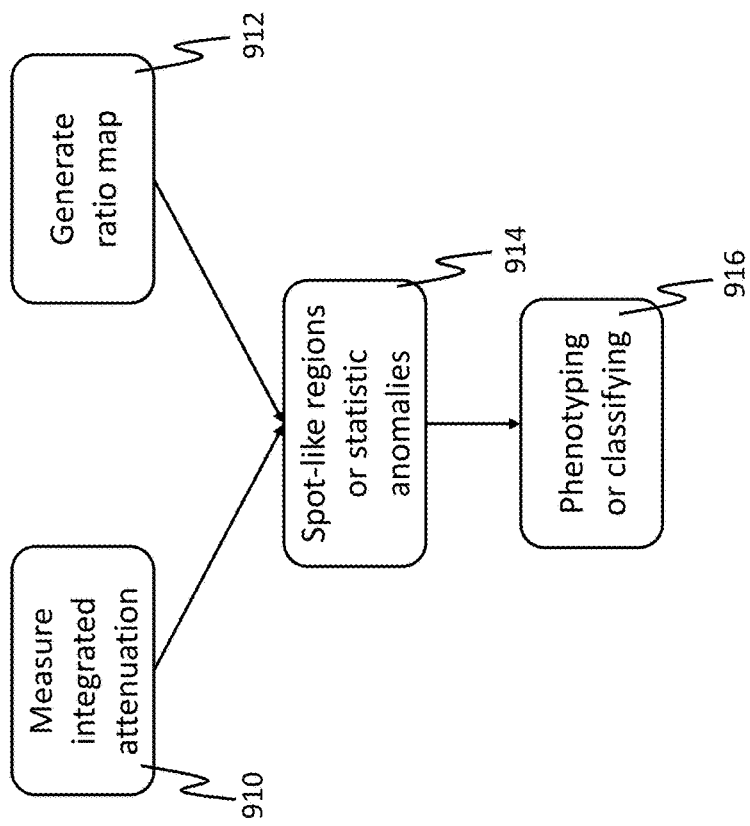
FIG. 9B illustrates a method of monitoring or classifying a disease based on measurements at a single point in time.

It is also noted that a phenotype could also be determined for just a single measurement. For example, as illustrated in FIG. 9B, a single integrated attenuation coefficient is measured 910 and/or a ratio map is generated 912. Spot-like regions (as in GA) or maps with spatial standard deviations or pattern deviations exceeding a threshold level may be noted 914, based on the single measurement. Based on these notations, the subject may be phenotyped and/or the disease classified 916, as described above. Additionally, it is noted that such a method is not limited to AMD and may be useful for other retinal conditions that affect the RPE integrity.

While the above methods were described as automated procedures (e.g., using a processor), it should be noted that full automation of the methods described herein is not intended to be limiting. Rather, in some embodiments, the methods may be entirely manual. Semi-automated embodiments are also envisioned to be within the scope of the present disclosure. For example, one semi-automated embodiment may additionally include a manual correction step(s).

The various embodiments described herein refer to imaging data of an eye obtained from OCT systems. However, the disclosed techniques and processes may equally apply to imaging data obtained using other types of imaging devices, for example ultrasound. Additionally, the disclosed techniques and processes may equally apply to any biological tissues, in addition to those in the eye, for which meaningful layers may be defined, segmented, and imaged as described herein.

It is to be noted that the above aspects, embodiments, and examples are envisioned to be implemented automatically by a processor. A "processor" as used herein refers to any, or part of any, electrical circuit comprised of any number of electrical components, including, for example, resistors, transistors, capacitors, inductors, and the like. The circuit may be of any form, including, for example, an integrated circuit, a set of integrated circuits, a microcontroller, a microprocessor, a collection of discrete electronic components on a printed circuit board (PCB) or the like. The processor may also stand alone or be part of a computer used for operations other than processing image data. It should be noted that the above description is non-limiting, and the examples are but only a few of many possible processors envisioned.

What is claimed is:

1. A method of processing ophthalmic image data comprising:
   obtaining optical coherence tomography (OCT) data of a subject's eye, the OCT data including data beyond the retinal pigment epithelium (RPE) of a subject's eye and intensities of an imaging signal as the imaging signal is backscattered by each of a plurality of tissue layers in the subject's eye;
   determining a ratio of the intensities of the backscattered imaging signal, the ratio being the intensity of a first portion of the backscattered imaging signal corresponding to at least a portion of a retinal layer with respect to the intensity of a second portion of the backscattered imaging signal corresponding to at least a portion of a sub-RPE layer;
   determining a representative value based at least in part on the determined ratio; and
   phenotyping or classifying the subject based at least in part on the determined representative value.

2. The method of claim 1, wherein
   the OCT data is captured at a plurality of times,
   a ratio and representative value are determined for the OCT data captured at each of the plurality of times, and
   the subject is phenotyped or classified based at least in part on a change in the determined ratios and/or representative values at the plurality of times.

3. The method of claim 2, wherein the change in the representative values and/or ratios is determined by performing a statistical measurement between the representative values and/or ratios at a first time of the plurality of times and the representative values and/or ratios and a second time of the plurality of times.

4. The method of claim 2, wherein the representative values and/or ratios at a first time of the plurality of times are registered with representative values and/or ratios at a second time of the plurality of times.

5. The method of claim 2, wherein the method further comprises:
identifying regions of the subject's eye based at least in part on a change in the determined ratios and/or representative values at the plurality of times.

6. The method of claim 1, wherein the subject is phenotyped or classified based at least in part on detecting spot-like regions or statistical anomalies in representative values and/or ratios determined for OCT data obtained for a plurality of axial scans.

7. The method of claim 6, wherein the spot-like regions are determined by comparing spatial standard deviations or pattern deviations to a threshold level.

8. The method of claim 1, further comprising:
applying a curve fitting technique to model a boundary traversing the bottom of the RPE based on pixels determined to correspond to the RPE; and
selecting the sub-RPE region based at least in part on the boundary.

9. The method of claim 1, wherein the representative value is selected from the group consisting of: attenuation coefficients, integrated attenuation, or a monotonic or near-monotonic proxy measurement.

10. The method of claim 1, wherein the method further comprises:
identifying diseased areas of the subject's eye based at least in part on the determined ratio or representative values.

11. The method of claim 1, wherein the imaging signal has a center wavelength of at least 1 µm.

12. The method of claim 1, wherein the retinal layer, portion of the retinal layer, combination of retinal layers, sub-RPE layer, portion of a sub-RPE layer, or combination of sub-RPE layers is determined using polarization sensitive optical coherence tomography (PS-OCT).

13. A method of processing ophthalmic image data comprising:
obtaining optical coherence tomography (OCT) data of a subject's eye for each of a plurality of axial scans, the OCT data including data beyond the retinal pigment epithelium (RPE) of a subject's eye and intensities of an imaging signal as the imaging signal is backscattered by each of a plurality of tissue layers in the subject's eye;
determining a ratio of the intensities of the backscattered imaging signal, the ratio being the intensity of a first portion of the backscattered imaging signal corresponding to at least a portion of a retinal layer with respect to the intensity of a second portion of the backscattered imaging signal corresponding to at least a portion of a sub-RPE layer, for each of the plurality of axial scans;
determining a representative value based at least in part on the determined ratio for each of the plurality of axial scans;
generating a map of the representative values, ratios, the intensities of the first portion of the backscattered imaging signal, or the intensities of the second portion of the backscattered imaging signal; and
phenotyping or classifying the subject based at least in part on the generated map.

14. The method of claim 13, wherein:
the OCT data is captured at a plurality of times,
the map is generated for the OCT data captured at each of the plurality of times, and
the subject is phenotyped or classified based at least in part on a change in the generated maps at the plurality of times.

15. The method of claim 14, wherein the change in the generated maps is determined by performing a statistical measurement between the representative values, ratios, intensities of the first portion, and/or intensities of the second portion at a first time of the plurality of times and the representative values and/or ratios and a second time of the plurality of times.

16. The method of claim 14, wherein the generated map at a first time of the plurality of times is registered with a generated map at a second time of the plurality of times.

17. The method of claim 14, wherein the method further comprises:
identifying regions of the subject's eye based at least in part on changes between the generated maps at the plurality of times.

18. The method of claim 13, wherein the subject is phenotyped or classified based at least in part on detecting spot-like regions or statistical anomalies in the generated maps.

19. The method of claim 18, wherein the spot-like regions are determined by comparing spatial standard deviations or pattern deviations to a threshold level.

20. The method of claim 13, further comprising:
applying a curve fitting technique to model a boundary traversing the bottom of the RPE based on pixels determined to correspond to the RPE; and
selecting the sub-RPE region based at least in part on the smooth boundary.

21. The method of claim 13, wherein the representative value is selected from the group consisting of: attenuation coefficients, integrated attenuation, or a monotonic or near-monotonic proxy measurement.

22. The method of claim 13, wherein the method further comprises:
identifying diseased areas of the subject's eye based at least in part on the generated map.

23. The method of claim 22, wherein the step of identifying diseased areas of the subject's eye further comprises:
generating seeds of diseased areas;
removing outliers of the generated seeds;
growing a region encompassed by the generated seeds that were not removed;
refining a contour of the grown regions;
identifying an area inside the contour as diseased; and
outputting the generated map with a contour around the regions identified as diseased or outputting a binary mask of the regions identified as diseased.

24. The method of claim 23, wherein the step of generating the seeds of diseased areas is performed by removing noise from the generated map and applying a thresholding technique on the generated map.

25. The method of claim 24, wherein the thresholding technique comprises finding an Otsu threshold of the generated map, comparing the Otsu threshold with a pre-set value, and selecting an intensity threshold based on the comparison, wherein the seeds of diseased areas are generated using pixels of the map that have intensities lower than the selected intensity threshold.

26. The method of claim 23, wherein the step of removing outliers is performed by grouping connected seed components and applying a distance analysis on the generated seeds.

27. The method of claim 13, wherein the imaging signal has a center wavelength of at least 1 μm.

28. The method of claim 13, wherein the retinal layer, portion of the retinal layer, combination of retinal layers, sub-RPE layer, portion of a sub-RPE layer, or combination of sub-RPE layers is determined using polarization sensitive optical coherence tomography (PS-OCT).

\* \* \* \* \*